(12) United States Patent
Chang et al.

(10) Patent No.: US 6,814,696 B1
(45) Date of Patent: *Nov. 9, 2004

(54) SURGICAL APPARATUS

(75) Inventors: Tenny Chang, Mountain View, CA (US); Charles Gresl, San Francisco, CA (US); Harry Ino, San Jose, CA (US); Liming Lau, Palo Alto, CA (US); John P. Lunsford, San Carlos, CA (US); Michael Wei, San Mateo, CA (US)

(73) Assignee: Origin Medsystems, Inc., Santa Clara, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 10/237,450

(22) Filed: Sep. 6, 2002

Related U.S. Application Data

(63) Continuation of application No. 09/560,636, filed on Apr. 28, 2000, now Pat. No. 6,471,638.

(51) Int. Cl.[7] .................................. A61B 1/00
(52) U.S. Cl. ................ 600/114; 600/104; 600/121; 604/264; 604/190
(58) Field of Search ................ 600/104–107, 600/114, 121, 127–129, 130, 135, 138, 153; 604/64.06, 264; 606/185, 190

(56) References Cited

U.S. PATENT DOCUMENTS

| | | | |
|---|---|---|---|
| 1,933,787 A | 11/1933 | Capstaff | |
| 3,224,320 A | 12/1965 | Knudsen | |
| 3,437,747 A | 4/1969 | Sheldon | |
| 3,556,085 A | 1/1971 | Takahashi et al. | |
| 4,319,563 A | 3/1982 | Kubota | |
| 4,630,598 A | 12/1986 | Bonnet | |
| 5,159,920 A | 11/1992 | Condon et al. | |
| 5,163,949 A | 11/1992 | Bonutti | |
| 5,271,380 A | 12/1993 | Riek et al. | |
| 5,334,150 A | 8/1994 | Kaali | |
| 5,385,572 A | 1/1995 | Nobles et al. | |
| 5,591,192 A | 1/1997 | Privitera et al. | |
| 5,722,934 A | * 3/1998 | Knight et al. | ............ 600/201 |
| 5,738,628 A | 4/1998 | Sierocuk et al. | |
| 5,980,549 A | 11/1999 | Chin | |
| 6,221,007 B1 | 4/2001 | Green | |

FOREIGN PATENT DOCUMENTS

| | | |
|---|---|---|
| EP | 0 347 140 A1 | 6/1989 |
| EP | 0 369 937 A | 11/1989 |
| EP | 0 642 764 A1 | 9/1994 |

* cited by examiner

*Primary Examiner*—John P. Leubecker
(74) *Attorney, Agent, or Firm*—Fenwick & West LLP

(57) ABSTRACT

An assembly of cannula and endoscope and dissection tip facilitate surgical procedures at remote surgical site in tissue of a patient. Relative rotation of the cannula about the endoscope from clamped rotational fixation of the cannula and endoscope is made possible by flexing a resilient clamping segment, and such relative rotation promotes convenient positioning of an eccentric tissue-dissecting tip about a vessel being harvested from within tissue of a patient. Color tinting of the tip or color-tinted illumination of tissue at a remote surgical site enhances contrasting visualization through the tip via the endoscope among the tissue types encountered at the surgical site within a patient. A tool bridge or lateral support mounts to a more rigid component such as an endoscope that extends from the proximal end of a cannula to support a more flexible surgical instrument also extending from the proximal end of the cannula.

1 Claim, 1 Drawing Sheet

SURGICAL APPARATUS

RELATED APPLICATION

This is a continuation of application Ser. No. 09/560,636, filed on Apr. 28, 2000, now U.S. Pat. No. 6,471,638, which is incorporated by reference herein in its entirety, and the subject matter of this application relates to the subject matter disclosed in U.S. patent application Ser. No. 09/227,393, filed on Jan. 8, 1999 by Albert K. Chin, now abandoned.

FIELD OF THE INVENTION

This invention relates to endoscopic surgical instruments and more particularly to components thereof to facilitate assembly of surgical instruments in sturdy and releasable configuration for convenient and safe manipulation during surgical procedures.

BACKGROUND OF THE INVENTION

Contemporary endoscopic surgical instruments commonly include an elongated shaft or cannula having multiple lumens extending therethrough from end to end for slidably positioning various surgical instruments therein to be manually manipulated from a proximal end of the cannula in order to affect various surgical procedures at the distal end. An endoscopic viewing instrument is usually included within one of such lumens, and bipolar scissors, or the like, may be disposed in another lumen through the elongated cannula to perform a surgical procedure within a field of view of the endoscope at the distal end of the cannula. The elongated cannula may be relatively rigid to provide adequate support for the endoscope over its entire length, and a surgical instrument such as bipolar scissors may exhibit some flexibility attributable to sufficiently small cross sectional area to slidably fit within a lumen of the elongated cannula. Such surgical instruments of sufficiently small cross sectional area to slide within a lumen of the cannula may undesirably flex and bend along a segment of its length not supported within the cannula as the cannula and the instruments assembled therein are manipulated relative to a surgical site on a patient, with concomitant breakage of the unsupported instruments.

In addition, a number of endoscopic instruments may be assembled within the narrow confines of the lumens within the cannula to fan out over a wider region near the proximal end in order to facilitate convenient mechanical attachment of video cameras, electrical and fluid connections, and the like. The proximal end of the cannula may be disposed within a supporting housing and the array of instruments and components within the cannula may be arranged to emanate from the housing at various locations and angles in order to avoid undesirable physical interference among instruments assembled about the proximal end of the cannula. An endoscope and associated video camera may be locked into position within the housing for proper rotational orientation relative to the cannula and housing, but may require quick disconnect mechanisms to facilitate rotational reorientation as desired during a surgical procedure. The distal end of the cannula commonly includes a tissue-dissecting tip for bluntly dissecting tissue within a visual field through the tip provided by the endoscope.

SUMMARY OF THE INVENTION

In accordance with one embodiment of the present invention, an instrument bridge is supported on a sturdy component assembled at the proximal end of a cannula to provide auxiliary support for less sturdy instruments that emanate from the proximal end at various angles and in spaced relationships about the proximal end of the cannula. In one embodiment of the present invention, a support member attaches to the cylindrical body of an endoscope and its associated video camera or detector at a location where the endoscope extends from the housing at the proximal end of the cannula. The support member protrudes laterally from the elongated axis of the endoscope to provide additional support for an endoscopic instrument of thin cross section, such as bipolar scissors. Specifically, the instrument bridge includes resilient clamps at opposite ends to resiliently grasp at the base end of the support the generally cylindrical barrel of an endoscope and to resiliently grasp at the lateral end of the support the generally cylindrical shape and narrow cross section of a surgical instrument. In this way, the surgical instrument of relatively narrow cross section and high flexibility is supported on and displaced away from the endoscope and endoscope attachments of relatively greater and more rigid cross section. In addition, the housing at the proximal end of the cannula may selectively lock and unlock the endoscope and associated video camera for selective rotational orientations within the housing. The base end of the support may also rotate about the barrel of the endoscope. The distal end of the cannula includes a transparent tip of blunt, eccentric conical shape to provide a relatively distortion-free field of view for the endoscope to facilitate blunt dissection of tissue, for example, along the course of a saphenous vein.

DETAILED DESCRIPTION OF THE INVENTION

Figure 1:
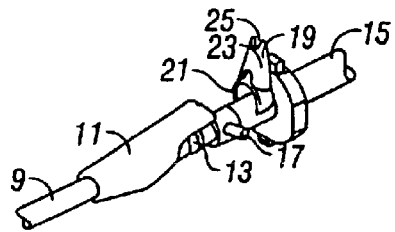
FIG. 1 is a perspective view of an endoscope emerging from a housing with an instrument support disposed thereon according to the present invention.

Referring now to FIG. 1, there is shown a perspective view of an elongated cannula 9 having a distal end (not shown) and a proximal end within housing 11. One lumen within cannula 9 extends between distal and proximal ends thereof and receives an endoscope 13 therein that facilitates the viewing of a surgical procedure at the distal end from the proximal end that extends from the housing 11. The endoscope 13 may include an eyepiece and an additional video detector 15 that attaches in axial alignment with the elongated optical axis of the endoscope 13. The body of the endoscope 13 that extends from the housing includes a lighting port 17 that may also be used conveniently, as later described herein, for rotationally orienting the endoscope 13 relative to the cannula 9 and housing 11.

In accordance with one embodiment of the present invention, an instrument bridge 19 includes a base clamp 21 attached to a lateral extension 23 that includes a smaller clamp or groove 25 at the distal end of the extension 23. The structure 21, 23, 25 may be formed of a resilient polymeric material such as polycarbonate, or the like, to provide flexibility and resilient clamping force in the base clamp 21 when disposed about the generally cylindrical body of the endoscope 13. The base clamp 21 may include a partial circumferential ring in excess of π radians and of about the same internal diameter as the cylindrical body of the endoscope 13 to promote snap-on clamping about the body of the endoscope 13. The internal diameter of the partial circumferential ring may be selected to fit snugly about the body of the endoscope 13, and to permit rotation of the instrument bridge 19 about the endoscope 13 as desired, for example, when rotating the cannula 9 about the endoscope 13.

Figure 2:
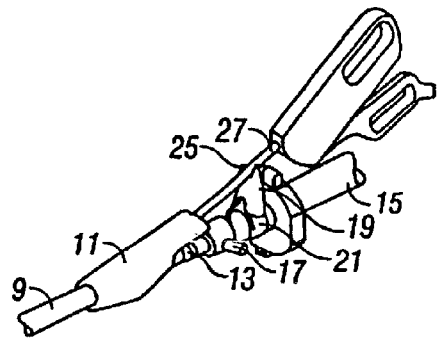
FIG. 2 is a perspective view of the embodiment of FIG. 1 showing a surgical instrument supported on the instrument support.

Thus, as illustrated in the perspective view of FIG. 2, an endoscopic surgical instrument 27 such as bipolar scissors having a small cross section over its elongated length for slidably and flexibly extending within a lumen of the cannula 9 between the ends thereof may 'fan' out or angle away from the elongated axis of the cannula at the proximal end thereof to be supported on the instrument bridge 19. Specifically, the clamp or groove 25 in the outer end of the lateral extension 23 of the instrument bridge 19 may firmly support the surgical instrument 27 therein, for example, via resilient clamping force about the cross section of the surgical instrument 27. The groove 25 may be formed in the resilient material of the instrument bridge 19 with smaller diameter than the diameter of the surgical instrument 27, and with a substantially circular interior shape in excess of π radian circumference to promote snap clamping of the surgical instrument 27 in position, as shown. Of course, the circular interior shape of groove 25 may be of about the same diameter as the diameter of the surgical instrument 27 where desired to promote rotational and sliding movement thereof within the groove 25.

Figure 3:
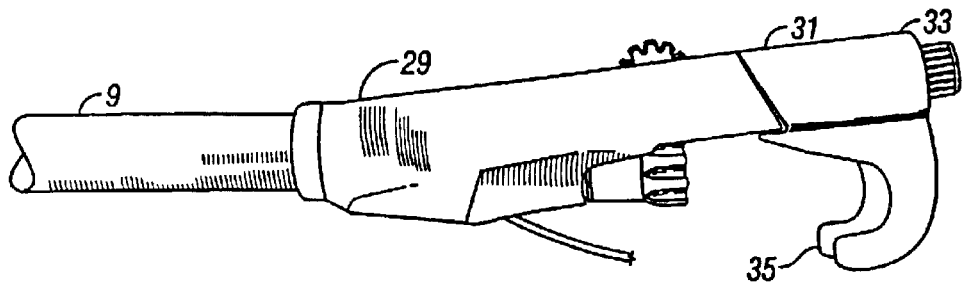
FIG. 3 is a front view of a housing and clamp for the instrument of FIG. 1.

As illustrated in FIGS. 1 and 2, an endoscope 13 may include an optical-fiber lighting channel for delivering illuminating light flux to the distal end of the endoscope within the cannula 9 from a light source (not shown) that attaches to the lighting port 17. This port is commonly rigidly affixed to the cylindrical body of the endoscope 13, for example, to contain input ends for optical fibers that channel light to the distal end of the endoscope. In one embodiment of the present invention, as illustrated in FIG. 3, the lighting port 17 may be clamped into lateral position relative to housing 29 by a hook-shaped clamping block 31 that may be selectively removed and attached to the housing 29 via hollow threaded fastener 33. This fastener 33 thus permits a surgical instrument such as bipolar scissors to be slidably and rotationally positioned within the cannula 9, and also facilitates selective attachment of the clamping block 31 to the housing 29. In a preferred embodiment of the invention, the hook-shaped segment 35 of the clamping block 31 (one on each side of the clamping block 31 to facilitate one aligned and one oppositely-aligned clamping positions of the lighting port 17) is formed sufficiently thin of flexible material such as polyethylene or other resilient polymeric material to be deflected or flexed out of clamping engagement with the lighting port 17. Specifically, the hook-shaped segment 35 is resilient and substantially semicircular with preferably less than π radian angular extent of the internal circumference about the diameter of the lighting port 17, as shown in FIG. 3. Thus, an endoscope disposed within the cannula and having a lighting port 17 disposed in clamped position relative to the housing 29 by the clamping block 31 may be conveniently twisted out of such clamped position without unscrewing the threaded fastener 33 by deflecting the resilient hook-shaped segment 35 out of locking engagement about the lighting port 17. In this way, an endoscope within cannula 9 may be rotationally re-positioned relative to the cannula and the surgical instruments assembled therein in shorter time than is normally required to unscrew the threaded fastener 33 to release the clamping block 31 disposed about lighting port 17 of the endoscope.

Figure 4:
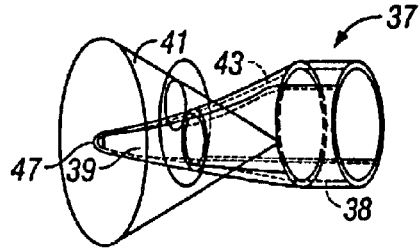
FIG. 4 is a perspective view of a tissue-dissecting tip of one configuration according to the present invention.
Figure 5:
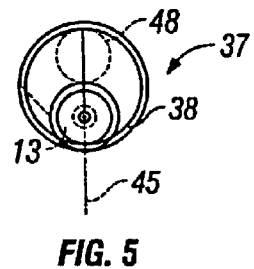
FIG. 5 is an end view of the tip according to FIG. 4.
Figure 6:
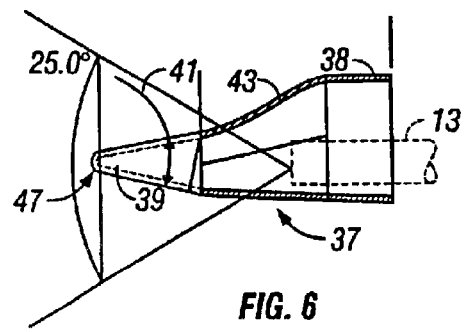
FIG. 6 is a side sectional view of the tip of FIG. 4.

Referring now to FIG. 4, there is shown a perspective view of a transparent tip 37 for attachment to the distal end of a cannula 9 to facilitate a surgical procedure such as blunt tissue dissection at a remote surgical site in a patient's body. Specifically, the transparent tip 37 includes a rearward section 38 that is disposed to attach (e.g., via press-fit, or adhesive attachment, or the like) to the distal end of a cannula, and includes a substantially conical forward section 39 that aligns with an endoscope within the cannula. The forward section 39 is displaced eccentrically from a cylindrical axis of the rearward section 38 to facilitate optical axial alignment with a field of view 41 of an endoscope 13 that is eccentrically oriented, as shown in the end view of FIG. 5, relative to an elongated central axis of a cannula attached to the rearward section 38 of the tip 37. The tip 37 includes a transition section 43 intermediate the forward section 39 and the rearward section 38 that includes tapering side walls in smooth transition between the conical walls of the forward section 39 and the circumferential side walls of the rearward section 38, as illustrated in side sectional view of FIG. 6. The forward section 39, intermediate section 43 and rearward section 38 of the tip 37 may be formed integrally and substantially symmetrically about a central vertical plane 45, as shown in FIGS. 4 and 5. The optical axis of the forward conical section 39 may thus be aligned with the field of view 41 of an endoscope disposed in eccentric orientation relative to the cylindrical axis of the rearward section 38 of the tip 37, as illustrated in the end view of FIG. 5.

In operation, the transparent tip 37 attached to the distal end of a cannula 9 protects an endoscope disposed therein from tissue and fluids and includes the transparent forward section of the tip 37 substantially optically aligned with the field of view of the endoscope. Thus, as the cannula is manipulated to perform a surgical procedure, for example, bluntly dissecting connective tissue from along a saphenous vein and around associated lateral branch vessels, the cannula 9 and attached tip 37 may be rotated about the elongated axis of the endoscope during tissue dissection along anterior and posterior segments of a saphenous vein to facilitate more complete dissection of connective tissue from the vein. And, such rotation of the cannula 9 about the endoscope may be conveniently accomplished by manually supplying rotational torque to the housing 29 relative to the endoscope 13 sufficiently to deflect the hook-shaped segment 35, as shown in FIG. 3, away from clamping engagement about the lighting port 17 of the endoscope 13. With the tip 37 removed from the distal end of the cannula 9, another lumen 48 of the cannula may be used to position therein a surgical instrument such as bipolar scissors 27 to facilitate excision and cauterization of lateral branch vessels encountered along the length of the saphenous vein.

The transparent tip 37 includes a blunt, slightly rounded distal end 47 of approximately 0.040" radius for bluntly dissecting tissue away from a saphenous vein and associated lateral branch vessels, and such tip may be formed of a bioinert, transparent material such as polycarbonate, glass, or the like, with conical walls of substantially uniform thickness in the forward section 39. Such conical shape in alignment with the optical axis of the endoscope reduces visual distortion in the field of view 41. However, the forward section 39 and intermediate section 43 may be formed in alternative configurations such as spoon shape or duck-bill shape or elliptical shape, or the like, to optimize the optical characteristics. The forward section 39 may be color tinted, at least within the field of view 41 of an endoscope to promote enhanced visual contrast between walls of a saphenous vein, connective tissue and blood encountered at a remote surgical site within a patient. It has been discovered that such color tinting at least of the forward section 39 within the spectral color range between yellow and blue tints enhances such visual contrast, with blue tint providing more effective visual contrast.

Therefore, the apparatus of the present invention promotes versatile and sturdy configurations of surgical instruments assembled within a cannula for performing surgical procedures at remote sites in tissue within a patient. An eccentric configuration of a blunt tip attached to the distal end of the cannula aligns with the optical axis of an endoscope that is positioned eccentrically therein to facilitate rotational manipulation of the cannula and attached tip about the endoscope. Also, the tissue-penetrating distal tip of small diameter aligned with an endoscope in one lumen significantly reduces the force required to dissect tissue away from the saphenous vein. Additionally, such tip of small diameter improves maneuverability around lateral branch vessels and along the saphenous vein in the lower leg within a thinner layer of subcutaneous fat. The transition cone between sections 38 and 39 transitions from these benefits of a small cone to the larger diameter of a two-lumen cannula without significantly diminishing the benefits of a small-diameter blunt dissection tip. Clamped fixation of the endoscope within a housing attached to the proximal end of the cannula may be conveniently overridden by deflecting a flexible hook-shaped segment of the clamp disposed about a lighting port of the endoscope in response to rotational torque applied to the housing relative to the endoscope. Color tinting of the transparent, tissue-dissecting tip serves as a rigid lens that promotes enhanced visual contrasts between tissue types encountered at remote surgical sites within a cavity in tissue of a patient. Such color tinted tip reduces glare reflected back from tissue and fluids and filters wavelengths of light transmitted back through the endoscope. A video detector attached to the proximal end of an endoscope may, with associated electronics of conventional design, provide further enhanced visual contrasts using 'white balance' electronic filtering to render the color tinting apparently clear while providing the desired visual contrasts and effects. Alternatively, a remote surgical site may be visualized through an endoscope as illuminated by color-tinted light supplied to the remote surgical site for similar benefits of enhanced contrasts between types of tissues encountered at the remote surgical site within a cavity in tissue of a patient.

What is claimed is:

1. Surgical apparatus comprising:

an elongated substantially cylindrical cannula including a plural number of lumens eccentrically oriented and extending therein between distal and proximal ends;

a housing attached to the cannula near the proximal end thereof including passages for slidably receiving therein surgical instruments including an endoscope disposed within one of the number of the lumens in the cannula; and a tissue-dissecting blunt tip having a cylindrical segment for attachment to the distal end of the cannula, the tip having a forward conical segment axially aligned with the eccentric orientation of the one lumen, and having an intermediate segment having exterior walls tapering between the cylindrical segment and the forward conical segment, at least the forward conical segment including transparent exterior walls that permit visualization therethrough by an endoscope within the one lumen.

\* \* \* \* \*